United States Patent
Hashimoto et al.

(10) Patent No.: US 8,070,795 B2
(45) Date of Patent: Dec. 6, 2011

(54) STENT WITH A JOINING PORTION AND A NON-JOINING PORTION FOR JOINING A STENT MAIN WIRE AND A STRUT

(75) Inventors: Yasushi Hashimoto, Utsunomiya (JP); Masaaki Matsutani, Utsunomiya (JP); Masatoshi Fukuda, Utsunomiya (JP)

(73) Assignee: Mani, Inc., Utsunomiya-shi, Tochigi (JP)

( * ) Notice: Subject to any disclaimer, the term of this patent is extended or adjusted under 35 U.S.C. 154(b) by 143 days.

(21) Appl. No.: 12/375,851

(22) PCT Filed: Jul. 6, 2007

(86) PCT No.: PCT/JP2007/063567
§ 371 (c)(1),
(2), (4) Date: Jan. 30, 2009

(87) PCT Pub. No.: WO2008/015873
PCT Pub. Date: Feb. 7, 2008

(65) Prior Publication Data
US 2009/0326637 A1 Dec. 31, 2009

(30) Foreign Application Priority Data
Aug. 2, 2006 (JP) ................. 2006-210540

(51) Int. Cl.
*A61F 2/06* (2006.01)
(52) U.S. Cl. ..................... 623/1.16; 623/1.2
(58) Field of Classification Search ........ 623/1.11–1.16, 623/1.2, 1.32, 2.14, 2.17; 606/194, 198, 606/200
See application file for complete search history.

(56) References Cited

U.S. PATENT DOCUMENTS

| | | | |
|---|---|---|---|
| 5,902,334 A * | 5/1999 | Dwyer et al. | 606/194 |
| 5,957,949 A | 9/1999 | Leonhardt et al. | |
| 6,123,723 A * | 9/2000 | Konya et al. | 623/1.11 |
| 6,890,350 B1 * | 5/2005 | Walak | 623/1.15 |
| 7,323,008 B2 * | 1/2008 | Kantor et al. | 623/1.15 |
| 7,794,492 B2 * | 9/2010 | Ishimaru et al. | 623/1.2 |
| 2005/0240257 A1 * | 10/2005 | Ishimaru et al. | 623/1.15 |
| 2006/0195177 A1 | 8/2006 | Kaufmann et al. | |

FOREIGN PATENT DOCUMENTS

| | | |
|---|---|---|
| JP | 63-199039 A | 8/1988 |
| JP | 2003-24334 A | 1/2003 |
| JP | 2003-62087 A | 3/2003 |
| JP | 2003062087 | * 3/2003 |

OTHER PUBLICATIONS

International Search Report issued in corresponding PCT application serial No. PCT/JP2007/063567.
Supplementary European Search Report issued in corresponding EPO Application No. 07 76 8299.

* cited by examiner

*Primary Examiner* — Tuan Nguyen
(74) *Attorney, Agent, or Firm* — Townsend & Banta

(57) ABSTRACT

A stent is provided, which joins a plurality of stent components via a strut which, even when repeatedly bent over a long period of time, resists breaking. In particular, a stent is provided having a joining portion which integrally joins a stent main wire and a strut, the stent main wire and the strut being fitted into a restraining pipe in a non-joining portion of the stent main wire and the strut near the end of the joining portion. This construction restrains the relative movement of the stent main wire to the strut 4 is restrained and decreased, thus reducing fatigue.

7 Claims, 3 Drawing Sheets

STENT WITH A JOINING PORTION AND A NON-JOINING PORTION FOR JOINING A STENT MAIN WIRE AND A STRUT

TECHNICAL FIELD

The present invention relates to a stent used for treating a tubular tissue represented by a blood vessel in the body. More specifically, the present invention relates to a stent in which a strut joined to a stent main wire maintains stable strength to improve reliability.

BACKGROUND ART

There are many tubular tissues, such as a blood vessel, a bile duct, a ureter, and an esophagus, in the body. A specific disease such as a stricture or occlusion can occur. A disease such as a stricture, occlusion, aneurysm, or varix can also occur in the blood vessel. In particular, the aneurysm is a serious disease to cause massive bleeding when the aneurysm is ruptured. The aneurysm need to be treated immediately. Various instruments have been developed to perform an effective treatment.

In recent years, a metal cylindrical instrument called a stent has been often used to treat the stricture or aneurysm in a blood vessel. To treat the stricture, the stent is housed in a sheath or catheter (hereinafter, called a sheath) and is then conveyed to an affected part. After reaching the affected part, the stent is removed from the sheath. The stent whose diameter is expanded by a balloon enlarges the stricture and is then indwelled for treatment. To treat an aortic aneurysm, a stent graft in which the stent is covered by an artificial blood vessel is indwelled in the aneurysm. The stent graft resists the pressure of blood. In this manner, the aneurysm is treated so as to prevent the action of the pressure thereon.

There are provided a mesh stent using a metal cylinder formed in mesh and, as described in Patent Documents 1 and 2, a loop stent using a loop, in which its overall shape is formed cylindrically by bending a wire in a round rod shape in a zigzag and then joining the ends of the wire.

As the stent which is indwelled in an affected part whose curved state and thickness are different between patients, there has been typically used a complex stent in which a plurality of loop stents are arranged in a longitudinal direction according to the curved state of the affected part and the loop stents are joined to each other by a wire called a strut.

As described in Patent Documents 1 and 2, a joining portion which joins the stent main wire and the strut of the stent is configured as follows. The stent main wire in a target portion of the loop stent is molded flat. The end of the strut is molded flat. The molding portions are overlapped with each other for being fitted into a pipe formed in a substantially rectangular shape. The pipe is then caulked.

The stent whose diameter is reduced is fitted into the sheath and is then conveyed to an affected part. Upon reaching the affected part, the stent is removed from the sheath. The diameter of the stent is expanded by the balloon or by itself. The stent whose diameter is expanded in the affected part is brought into contact with the inner wall surface of a blood vessel corresponding thereto, thereby treating the blood vessel.

Patent Document 1: Japanese Patent Application Laid-Open No. 2003-062087

Patent Document 2: Japanese Patent Application Laid-Open No. 2004-097382

DISCLOSURE OF THE INVENTION

The present inventors have conducted various examinations because the stent indwelled in an affected part need to maintain stable performance semipermanently. The examinations have been conducted by setting conditions which are more severe than those when the stent is indwelled and operated in the affected part.

The stent indwelled in the affected part does not always hold the same posture but is always changed with the activity of a body. From this perspective, a repeated bending examination is conducted on the stent having the plurality of loop stents joined by the strut as one of the examinations. As the result of the examination, it is found that the strut can be broken from the joining portion of the strut, the stent main wire being the starting point.

An object of the present invention is to provide a stent which cannot be broken when the repeated bending acts on the stent for a long period.

The present inventors have considered why the strut can be broken from the joining portion of the strut, the stent main wire being the starting point.

Both ends of the strut are joined to the different loop stents in a linear state. The ends become beam-like so as to be moved freely. The resistance to the acting bending is small. The stent can be bent from the joining portion of the strut and the stent main wire as the starting point. The repeated bending caused in the stent acts on the joining portion of the strut and the stent main wire, thereby causing fatigue. The strut is thus broken.

According to the consideration, the fatigue of the strut in the joining portion of the strut and the stent main wire is reduced to prevent the breaking of the strut. To reduce the fatigue of the strut, the bending angle of the strut in the joining portion is decreased to reduce the bending stress caused in the portion. The effect can thus be exerted.

To address the above problems, a stent according to the present invention which has a joining portion integrally joining a stent main wire and a strut, including a restraining means which restrains the stent main wire and the strut in a non-joining portion of the stent main wire and the strut near the end of the joining portion.

The stent according to the present invention includes the restraining means which restrains the stent main wire and the strut in the non-joining portion near the joining portion of the stent main wire and the strut. The bending of the strut relative to the stent main wire can be restrained by the restraining means. The bending angle of the strut relative to the stent main wire can be decreased.

Even if the repeated bending acts on the stent, the fatigue of the strut can be reduced to prevent the breaking due to the fatigue. The stent can have high reliability.

EXPLANATION OF REFERENCE NUMERALS

Figure 1:
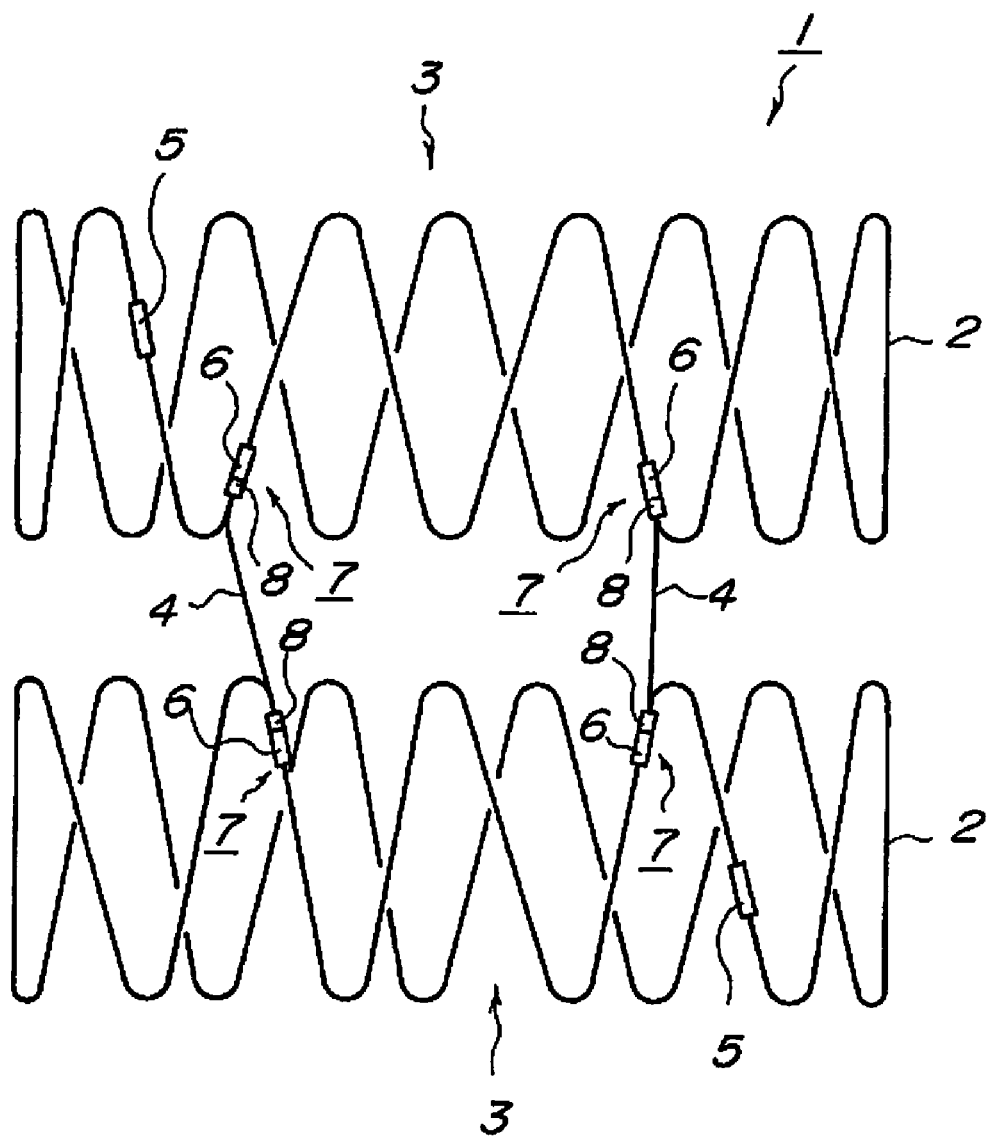
FIG. 1 is a diagram describing an example of the relation between a stent configured by joining a plurality of loop stents by a strut and a sheath.

1: Stent
2: Stent main wire
3: Loop stent
4: Strut
5: Protecting pipe
6: Joining pipe 6a to 6c: Unit pipe
6d: Auxiliary pipe
7: Joining portion
8: Restraining pipe
2a, 4a: Molding portion
2b, 4b: Non-molding portion

BEST MODE FOR CARRYING OUT THE INVENTION

A preferred embodiment of a stent according to the present invention will be described below. The stent according to the present invention is applied to a tubular tissue, such as a blood vessel, a bile duct, a ureter, or an esophagus, in a living body. If a disease such as a stricture or occlusion occurs in the tubular tissues, in particular, if an aneurysm or a varix occurs in the blood vessel, the stent is indwelled in an affected part and has the function of reinforcing the tubular tissue in the affected part.

The stent of the present invention is configured by joining a plurality of stent components (e.g., loop stents) made of metal wires in a round rod shape by a strut. The stent main wire configuring the stent component and the strut are integrally joined in a joining portion. In the present invention, the shape and configuration of the entire stent are not limited. The present invention limits that the stent has the plurality of stent components and that the stent components are integrally joined in the joining portion by the strut.

Whether the stent components are configured as the cylindrical stents or the loop stents does not matter. Instead, it matters whether or not the cylindrical stents and the loop stents configuring the stent are integrally joined by the strut. To prevent the description from being complicated, the stent of the present invention configured by used of the loop stents will be described below.

A metal wire in a round rod shape (stent main wire) is bent in a zigzag. Both end faces of the wire are butt welded or both ends thereof are fitted into a sleeve and are then caulked. By this, the outer shape of the loop stent is formed cylindrically. Both ends of the stent main wire are joined so as to be relatively non-rotatable. When the diameter of the loop stent having a predetermined shape is reduced and the loop stent is fitted into a sheath without being deformed. When being removed from the sheath to expand its diameter, the loop stent can be precisely returned to its original shape.

In the present invention, the material of the metal wire configuring the loop stent and the strut is not limited. Any metal which has moderate elasticity and flexibility and cannot affect a biotissue can be used. As such metal, there are metal wires of a stainless steel and a shape-memory alloy such as an Ni—Ti alloy. These materials can be used selectively.

As the material of the loop stent and the strut, it is preferred to use a wire which is made of an austenitic stainless steel having high reliability to biocompatibility. The wire made of an austenitic stainless steel and having a predetermined diameter is subjected to the cold wire drawing process at a predetermined reduction of area so as to extend its tissue in fiber form. The wire is preferable because it maintains moderate elasticity and flexibility for a long period and has high toughness.

In the present invention, the stent main wire configuring the loop stent and the strut are integrally joined in the joining portion. The configuration of the joining portion is not limited. Upon the action of an external force, the stent main wire and the strut may be joined without causing relative rotation, sliding, or separation. Such a joining portion can be a weld joining configuration and a caulking joining configuration. Any of these can be employed effectively.

The stent main wire and the strut are joined by welding. There are a method of spot welding the end of the strut overlapped with the stent main wire by irradiation of a laser beam in an overlapping direction, a method of spot welding the overlapped portion sandwiched between electrodes to turn on the electricity, and a method of welding the overlapped portion formed with a bead. The stent main wire and the strut can be joined using any of those methods.

In a case where the stent main wire and the strut are welded as described above, the welding portion and its periphery can be weak due to the influence of heat. For this reason, when the joining portion is formed by welding, it is preferred that the welding portion and its periphery be reinforced by a reinforcing pipe.

Next, a case where the stent main wire and the strut are joined by caulking is considered. In this case, when the loop stent is configured, a joining pipe is fitted over the stent main wire. The end of the strut is overlapped with the stent main wire. The joining pipe is fitted over the overlapped portion and is then caulked. Thus, the stent main wire and the strut can be joined.

As described above, when the stent main wire and the end of the strut are fitted into the joining pipe and are then joined by caulking the joining pipe, the sectional shape in the joining portion of the stent main wire and the strut is not limited. The sectional shape can be of any shape such as a circle, a flat square, or other shapes. It is preferred that the sectional shape be set, if necessary, according to the conditions required for the joining portion which allow the joining portion to be relatively rotatable or non-rotatable.

The portion of the stent main wire corresponding to the joining portion and the end of the strut are both molded flat. The joining pipe is formed in a substantially rectangular shape. The flat portions are fitted into the joining pipe and are then caulked. The stent main wire and the strut can be joined so as to be relatively non-rotatable. The sections of the stent main wire and the strut are circular. In such a case, the joining pipe is formed to be elliptical by flattening a circular shape. The circular portion is fitted into the joining pipe and is then caulked. The stent main wire and the strut can be joined so as to be allowed to be relatively rotatable.

The length of the joining pipe is not limited and may be a length which can reliably join the stent main wire and the strut. After the loop stent is manufactured, the linear component is joined to the loop stent. The joining pipe is fitted over the stent main wire before the end faces of the loop stent are welded. The joining pipe need to smoothly pass over the bending portion of the zigzag formed in the loop stent.

The joining pipe can be configured by one pipe. The joining pipe can be preferably configured by a plurality of unit pipes which are short and are formed so as to easily pass over the bending portion of the zigzag. According to the present invention, the joining pipe is not always configured by one pipe and can be configured by integrally joining the plurality of unit pipes.

The material of the joining pipe is not limited. Any material which cannot affect a living body, which is deformed according to an acting caulking force, and which can maintain sufficient strength for a long period, can be used. As such a joining pipe, a pipe made of austenitic stainless steel is preferably used.

In the present invention, a restraining means is provided in a non-joining portion near the joining portion of the stent main wire and the strut and restrains the stent main wire and the strut to reduce the fatigue of the strut.

By the restraining means provided in the non-joining portion near the joining portion of the stent main wire and the strut, the restraining means and the joining portion support the bending of the strut. The stress caused in the strut with the bending is dispersed in the joining portion and the restraining portion of the restraining means. The stress caused in the portion corresponding to the joining portion is decreased to realize reduction of the fatigue.

The restraining of the stent main wire and the strut by the restraining means does not integrate both firmly and restrains the amount of movement while allowing the stent main wire and the strut to be relatively moved away from each other and moved towards each other. The restraining means can be of any configuration and shape, if a restraining function can be exerted.

As the restraining means having the above function, there are a pipe fitted over the overlapped portion of the stent main wire and the strut with a fit tolerance to an extent of a loose fit, a pipe made of a soft resin that cannot affect a biotissue, a binding slightly loosened by a wire or string, and a similar configuration. In the present invention, the function of the restraining means is limited, but the configuration thereof is not limited.

In the present invention, the restraining means is provided in the non-joining portion near the joining portion. The distance between the locating position of the restraining means and the joining portion is not limited. The restraining means may support and restrain the bent strut and may be arranged in a position where the bending angle of the strut at the end of the joining portion can be decreased.

The sectional shapes of the stent main wire and the strut in the joining portion are molded flat. If they are molded such as to expose the boundary portion between the molding portion and the non-molding portion of the wire, it is preferred that the restraining means be arranged closer to the non-molding portion of the wire than the boundary portion. As seen from the above, the sectional shape of the joining portion can be different from that of other portions. In such case, the restraining means is arranged in the non-molding portion. This prevents the concentration of stress onto the boundary portion between the molding portion and the non-molding portion of the strut. Accordingly, reduction of fatigue can be realized.

Embodiment 1

Figure 2:
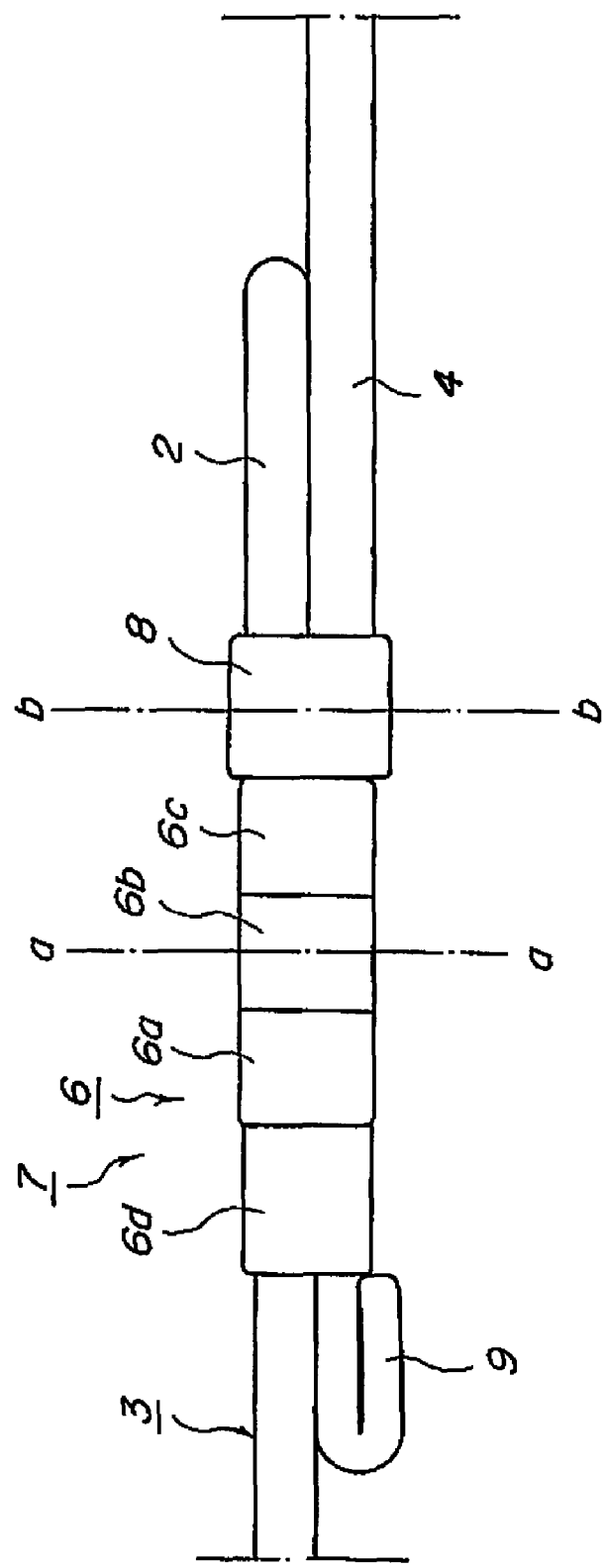
FIG. 2 is a diagram describing the configuration of a joining portion of a stent main wire and the strut and the relation between the joining portion and a restraining means.
Figure 3B:
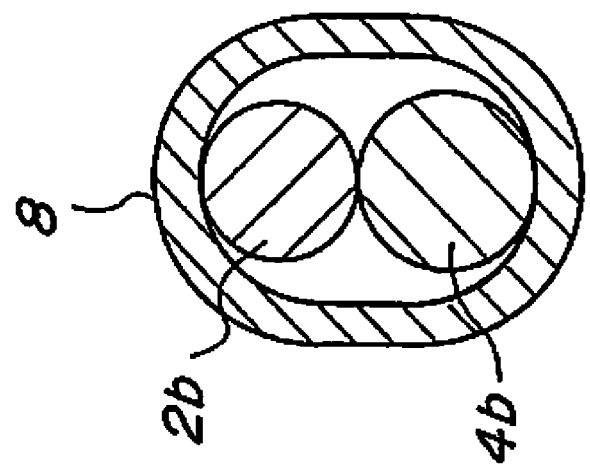
FIGS. 3(a) and 3(b) are diagrams describing the sectional shapes of essential parts of FIG. 2.
Figure 3A:
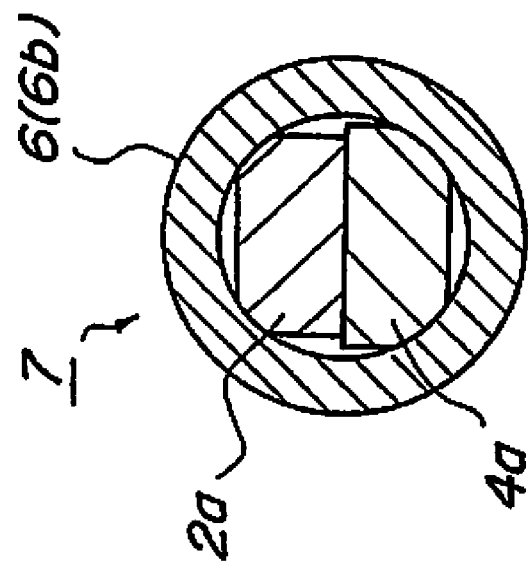

An embodiment of a stent according to the present invention will be described with reference to the drawings. FIG. 1 is a diagram describing an example of the relation between the stent configured by joining a plurality of loop stents with a strut and a sheath. FIG. 2 is a diagram describing the configuration of a joining portion and a restraining means. FIGS. 3(a) and 3(b) are cross-sectional views of essential parts of FIG. 2.

As illustrated in FIG. 1, a stent 1 according to this embodiment is a complex stent in which a plurality of loop stents 3 which are formed to be loop-like by bending stent main wires 2 in a zigzag and butt welding, and in which the end faces of the stent main wires 2 are arranged in series and are then joined by at least two struts 4.

In the butt welding portion of the stent main wire 2 of the loop stent 3 and the vicinity thereof, an austenitic tissue extended in fiber form becomes a particulate tissue which is bulky under the influence of heat by welding. The strength is thus lowered. For this reason, a protecting pipe 5 is arranged in the welding portion and the vicinity thereof, so that the deteriorated portion by welding is reinforced by the protecting pipe 5.

The loop stent 3 and the strut 4 are fitted into a joining pipe 6. The joining pipe 6 is caulked to configure a joining portion 7. A restraining pipe 8 configuring the restraining means is arranged close to the joining pipe 6 installed in the joining portion 7. The stent main wire 2 and the strut 4 are restrained by the restraining pipe 8.

As the stent main wire 2 configuring the loop stent 3, there is used a material in which a wire made of an austenitic stainless steel, in particular, a wire made of SUS316L preferably used as an implanting stainless steel, is subjected to the cold wire drawing process to extend its tissue in fiber form, thereby exerting work hardening and improving the mechanical properties. The loop stent 3 configured by such a material may have good biocompatibility and can exert a moderate extending force. When reaching a target affected part and being removed from the sheath, accordingly, the stent is returned to its original shape to reinforce the affected part for a long period.

Like the stent main wire 2, there is used, for the strut 4, a material obtained by subjecting a wire made of an austenitic stainless steel, in particular, a wire made of SUS316L, to the cold wire drawing process to extend its tissue in fiber form.

The thickness of the wire configuring the loop stent 3 and the strut 4 is different according to an organ in which the stent is to be indwelled. In this embodiment, the stent main wire of the loop stent 3 has a diameter of about 0.4 to 0.5 mm. As can be seen, the strut 4 has a diameter of about 0.5 mm. The strut 4 has a thickness slightly larger than that of the stent main wire 2 configuring the stent 3. This is intended to increase the rigidity of the strut 4 to maintain the shape. The stent can resist the fatigue due to the repeated bending caused in the strut 4, accordingly.

As in the stent main wire 2, the protecting pipe 5, the joining pipe 6, and the restraining pipe 8 are made of SUS316L preferably used as an implanting stainless steel. The protecting pipe 5 and the joining pipe 6 are caulked, thus are not hardened before use.

The restraining pipe 8 is not caulked. Instead, there is used a material which is softened sufficiently so as to allow the strut 4 to be moved away from and moved towards the stent main wire 2 with the repeated bending which acts on the stent 1.

The protecting pipe 5 is fitted over the stent main wire 2 immediately before butt welding of the stent main wire 2 formed in a zigzag. The protecting pipe 5 is formed of one pipe which has a length sufficient to protect the welding portion.

After the stent main wire 2 is formed zigzag, the joining pipe 6 and the restraining pipe 8 are fitted over the stent main wire 2 before the ends of the stent main wire 2 are welded. The joining pipe 6 and the restraining pipe 8 need to have a length which can easily pass over the minimum radius portion of the stent main wire 2 formed in a zigzag (the bending portion of the zigzag).

The joining pipe 6 has the function of firmly joining the stent main wire 2 and the strut 4 and need to have a moderate length to reliably join both. The joining pipe 6 is configured by integrally joining a plurality of unit pipes having a short length which can pass over the minimum radius portion of the stent main wire 2. When the diameter of the stent main wire 2 is 0.45 mm, the length of the unit pipe configuring the joining pipe 6 is set to 0.98 mm. The three unit pipes are integrally joined to configure the joining pipe 6.

The restraining pipe 8 also has a short length which can pass over the minimum radius portion of the stent main wire 2. To exert the function of the restraining means, the length need not be long. The restraining pipe 8 has a length substantially equal to or slightly longer than the length of the unit pipe configuring the joining pipe 6.

The configuration of the joining portion and the configuration of the restraining means of the stent 1 will be described by FIGS. 2 and 3.

The joining portion 7 of the stent 1 according to this embodiment is configured by fitting and caulking the stent main wire 2 of the loop stent 3 and the strut 4 into the joining pipe 6. The restraining pipe 8 is provided adjacent to the joining pipe 6. The restraining means is configured by the restraining pipe 8.

The stent main wire 2 and the strut 4 are configured using the wire in which a wire of SUS316L is subjected to the cold wire drawing process and its tissue is extended in fiber form. The joining pipe 6 and the restraining pipe 8 are also made of SUS316L.

The restraining pipe 8 allows the stent main wire 2 and the strut 4 to be relatively moved away from each other and moved towards each other, thereby restraining the movement of both. The restraining pipe 8 having a wall thickness thinner than that of the joining pipe 6 is softened by annealing.

The joining pipe 6 has three unit pipes 6a to 6c having the same size and material, and an auxiliary pipe 6d arranged at the end of the strut 4 in a longitudinal direction of the unit pipes 6a to 6c. The auxiliary pipe 6d is provided to avoid the stress concentration on the stent main wire 2 and the strut 4 which are flattened. The pipes 6a to 6d are fitted over the stent main wire 2 of the loop stent 3 and are moved to the position of the joining portion 7 joining the strut 4 along the stent main wire 2.

The restraining pipe 8 is arranged on the opposite side of the auxiliary pipe 6d in a longitudinal direction of the joining pipe 6. The pipes 6a to 6d configuring the joining pipe 6 and the restraining pipe 8 are fitted over the stent main wire 2 by holding a predetermined order and are moved along the stent main wire 2 to the joining portion 7 of the strut 4.

In this embodiment, the sections of the stent main wire 2 and the strut 4 are molded flat by pressing in the positions corresponding to the joining portion 7. As illustrated in FIG. 3(a), flat molding portions 2a and 4a are formed in the stent main wire 2 and the strut 4. The pipes 6a to 6d configuring the joining pipe 6 are configured as substantially rectangular pipes which have the same section as that of the shape in which the molding portion 2a of the stent main wire 2 and the molding portion 4a of the strut 4 are overlapped.

The sectional shape of the joining pipe 6 need not be precisely rectangular and may have a shape into which the overlapped portion of the molding portion 2a of the stent main wire 2 and the molding portion 4a of the strut 4 are fitted. The outer shape of the joining pipe 6 need not be precisely rectangular at all and may be a shape preferable for caulking, e.g., a shape in which a corner portion has a curved surface.

Non-molding portion 2b having the same shape as the section of the stent main wire 2 is formed on either side in a longitudinal direction of the molding portion 2a of the stent main wire 2. The molding portion 4a is formed in the strut 4 in the portion corresponding to the joining pipe 6. The molding portion 4a is formed continuously to the end. A non-molding portion 4b having the same shape as the section of the material of the strut 4 is formed on the opposite side of the end (see FIG. 3(b)).

The molding portion 2a of the stent main wire 2 and the molding portion 4a of the strut 4 are fitted into the unit pipes 6a to 6c configuring the joining pipe 6. The auxiliary pipe 6d is fitted over the molding portions 2a and 4a or is fitted over the boundary portion between the molding portion 2a and the non-molding portion 2b of the stent main wire 2 and the molding portion 4a of the strut 4.

The unit pipes 6a to 6c and the auxiliary pipe 6d configuring the joining pipe 6 are caulked. As illustrated in FIG. 3(a), the sectional shape of the joining pipe 6 is molded in a substantially circular shape. With this, the molding portion 2a of the stent main wire 2 and the molding portion 4a of the strut 4 are molded. The stent main wire 2 and the strut 4 are joined integrally.

The restraining pipe 8 is arranged so as to be integrally joined to the joining portion 7 which is joined by the joining pipe 6. The restraining means is configured by the restraining pipe 8. Specifically, the restraining pipe 8 is arranged so as to be integrally joined to the joining pipe 6 and is fitted over the non-molding portion 2b of the stent main wire 2 and the non-molding portion 4b of the strut 4.

The restraining pipe 8 is fitted over the non-molding portion 2b of the stent main wire 2 and the non-molding portion 4b of the strut 4. The sectional shape of the restraining pipe 8 is formed in a substantially ellipse shape and is not subjected to special caulking. The arranging position can be shifted. Specifically, the restraining pipe 8 is arranged in the predetermined position integrally joined to the joining pipe 6. The restraining pipe 8 is then deformed by a light manual force to secure the arranging position.

In the stent 1, the restraining pipe 8 is fitted over the non-molding portion 2a of the stent main wire 2 and the non-molding portion 4a of the strut 4 near the joining portion 7 to configure the restraining means. The repeated bending acts on the stent 1. With this, the strut 4 is bent from the joining portion 7 of the strut 4, the stent main wire 2 being the starting point. The bending is supported by the restraining pipe 8. The bending angle at the joining portion 7 as the starting point can be decreased.

The bending stress acting on the starting point of the joining portion 7 of the strut 4 (the portion corresponding to the end of the joining pipe 6) can be decreased. The fatigue can thus be reduced. The breaking of the strut 4 from the joining portion 7 as the starting point due to the fatigue can be prevented.

In this embodiment, the case of using the restraining pipe 8 as the restraining means is described. As described above, the present invention does not limit the configuration of the restraining means. The bending of the strut 4 relative to the stent main wire 2 with repeated bending acting on the stent 1 may be restrained to reduce the fatigue of the joining portion 7.

In this embodiment, a predetermined length range of the end of the strut 4 is softened by annealing. The end of the strut 4 is fitted into the restraining pipe 8 and the joining pipe 6 along the stent main wire 2 so as to be protruded from the joining pipe 6. The end is folded back 180° to form a folding-back portion 9. The folding-back portion 9 engages the end face of the auxiliary pipe 6d of the joining pipe 6 to prevent the folding-back portion 9 from falling off the joining pipe 6.

INDUSTRIAL APPLICABILITY

After the stent 1 according to the present invention is indwelled in an affected part, upon the action of the repeated bending on the stent 1 with the activity of a human, the breaking of the strut due to the fatigue caused therein can be prevented. The stent indwelled in the body for a long period can exert high reliability.

The invention claimed is:
1. A stent which has a joining portion integrally joining a stent main wire and a strut, characteristic in that said stent comprises a restraining means which restrains the stent main wire and the strut in a non-joining portion of the stent main wire and the strut near an end of the joining portion while allowing the stent main wire and the strut to be relatively moved away from each other and moved towards each other with a repeated bending which acts on the strut.

2. A stent comprising:

a stent main wire;

a strut, a joining portion disposed around the stent main wire and the strut so as to integrally join the stent main wire and the strut, said joining portion having a first end and a second end; and a restraining pipe disposed around the stent main wire and the strut adjacent the second end of the joining portion, wherein the restraining pipe restrains the stent main wire and the strut in a non-joining manner under repeated bending forces exerted upon the strut and distributing stress along a length of the restraining pipe, thereby reducing fatigue on the second end of the joining portion.

3. The stent of claim 2, wherein the joining portion is comprised of an auxiliary pipe at the first end thereof, and two or more unit pipes disposed adjacent to the auxiliary pipe.

4. The stent of claim 3, wherein the restraining pipe has a length equal to or slightly longer than one of the two or more unit pipes.

5. The stent of claim 2, wherein the stent main wire and the strut are molded flat in an area adjacent the unit pipes of the joining portion.

6. The stent of claim 3, wherein the auxiliary pipe and the units pipes are substantially rectangular.

7. The stent of claim 2, wherein a folding back portion is formed in an end of the strut, adjacent to the joining portion, said folding back portion preventing the strut from disengaging from the joining portion.

* * * * *